(12) United States Patent
Pouget et al.

(10) Patent No.: US 6,852,096 B1
(45) Date of Patent: Feb. 8, 2005

(54) DISPOSABLE HYPODERMIC SYRINGE WITH LOCKING PROTECTIVE SHEATH

(75) Inventors: Michel Pouget, Domarin (FR); Fabrice Bonacci, Saint Priest (FR)

(73) Assignee: Compagnie Plastic Omnium, Lyons (FR)

( * ) Notice: Subject to any disclaimer, the term of this patent is extended or adjusted under 35 U.S.C. 154(b) by 0 days.

(21) Appl. No.: 10/111,094

(22) PCT Filed: Oct. 26, 2000

(86) PCT No.: PCT/FR00/02987

§ 371 (c)(1),
(2), (4) Date: Jun. 19, 2002

(87) PCT Pub. No.: WO01/30428

PCT Pub. Date: May 3, 2001

(30) Foreign Application Priority Data

Oct. 26, 1999 (FR) .............................. 99 13347

(51) Int. Cl.$^7$ ............................. A61M 5/30; A61M 5/32
(52) U.S. Cl. ...................................... 604/110; 604/198
(58) Field of Search ................................ 604/110, 192, 604/198, 195, 187, 263, 193

(56) References Cited

U.S. PATENT DOCUMENTS

| 5,433,712 A | 7/1995 | Stiles et al. |
| 5,562,626 A | 10/1996 | Sanpietro |
| 6,186,980 B1 * | 2/2001 | Brunel .................. 604/110 |
| 6,319,233 B1 * | 11/2001 | Jansen et al. ............ 604/192 |

FOREIGN PATENT DOCUMENTS

| EP | 0 680 767 A1 | 11/1995 |
| FR | WO 00/76565 | * 12/2000 |
| WO | WO 93/00949 A1 | 1/1993 |

\* cited by examiner

*Primary Examiner*—Nicholas D. Lucchesi
*Assistant Examiner*—Matthew DeSanto
(74) *Attorney, Agent, or Firm*—Oliff & Berridge, PLC

(57) ABSTRACT

Safety device for a syringe is constituted by a body, a needle carrier, a piston, and a piston plunger. The device includes a sheath and a body. The syringe body may slide axially inside the sheath between an injection position and a safe position. A return member urges the syringe body towards the safe position, and may be triggered automatically when the piston plunger is pushed into the body. A telescopic head is capable of taking up a retracted position and an extended position. A combination for locking the telescopic head in the extended position may be constituted by a combination of two oppositely-directed axial bearing surfaces bearing against two oppositely-directed axial bearing surfaces of the sheath, and two oppositely-directed lateral bearing surfaces which bear against two oppositely-directed lateral bearing surfaces of the sheath.

6 Claims, 1 Drawing Sheet

DISPOSABLE HYPODERMIC SYRINGE WITH LOCKING PROTECTIVE SHEATH

The present invention relates to a syringe safety device which is provided with a telescopic head.

BACKGROUND OF THE INVENTION

It is known that certain injectable medicines are distributed in doses in prefilled syringes to which it is necessary merely to add piston plungers and needles in order to be able to use them.

It is also known that used syringes are dangerous, in particular for medical personnel, since once it has been used, the needle of a syringe is dirtied and potentially contaminating for people who come into contact with the needle or who prick themselves accidentally.

OBJECTS AND SUMMARY OF THE INVENTION

The present invention seeks to provide a safety device which avoids any risk of injury or pricking with the needle of a syringe that has already been used to inject a substance.

The present invention provides a safety device for a syringe constituted by a body, a needle carrier mounted at one end of the body, a piston movable inside the body, and a piston plunger projecting from the body at its end opposite from the needle carrier and suitable for pushing the piston into the body towards the needle carrier, the device comprising a sheath having a front end and a rear end, the syringe body being capable of sliding axially inside the sheath between an injection position in which the syringe body is fully contained within the sheath while the needle carrier of the syringe is flush with the front end of the sheath, and a safe position in which a portion of the syringe body projects from the rear end of the sheath while the needle carrier is set back from the front end of the sheath, the device also comprising a return member urging the syringe body towards the safe position, which return member is triggered automatically when the piston plunger is pushed into the body of the syringe, the rear end of the sheath having a telescopic head capable of taking up a retracted position in which it does not act on the syringe body when in the injection position, and an extended position in which it surrounds the portion of the syringe body that projects from the rear end of the sheath when in the safe position, the device further comprising locking means for locking the telescopic head in the extended position, said locking means being constituted by a combination of two oppositely-directed axial bearing surfaces of the telescopic head which bear against two oppositely-directed axial bearing surfaces of the sheath, and of two oppositely-directed lateral bearing surfaces of the telescopic head which bear against two oppositely-directed lateral bearing surfaces of the sheath.

By means of the device of the invention, once the substance has been injected, the return member causes the syringe body to rise into the sheath into the safe position, thereby causing the syringe needle to be retracted into the sheath.

Any accidental contact with the needle then becomes impossible.

Because the sheath's telescopic head, when in the extended position, covers the portion of the syringe body that projects beyond the rear end of the sheath, the syringe is held in the sheath and cannot escape therefrom via its rear end.

In the invention, when the telescopic head is in the extended position, it is securely fastened to the sheath by mutual thrust between the two oppositely-directed axial bearing surfaces of the sheath on the two oppositely-directed axial bearing surfaces of the head, in combination with mutual thrust between the two oppositely-directed lateral bearing surfaces of the sheath on the two oppositely-directed lateral bearings surfaces of the head.

The axial bearing surfaces prevent the telescopic head from moving axially relative to the sheath.

The function of the lateral bearing surfaces is to keep the axial bearing surfaces against one another even in the event of the head of the sheath being slightly deformed radially, so as to ensure that axial locking of the head relative to the sheath is not interrupted by exerting pressure sideways on the head or on the sheath.

In other words, in the safety device of the invention, if the telescopic head or the sheath is subjected to stress perpendicularly to the axis of the device, the resulting radial deformation of the telescopic head or of the sheath does not in any way release the head axially relative to the sheath.

In a particular embodiment of the invention, the syringe body is prevented from moving axially relative to the sheath by means of the telescopic head.

In this embodiment, the syringe body is held in the safe position relative to the telescopic head which, as explained above, is securely fastened axially relative to the sheath, in accordance with the invention.

In another embodiment of the invention, the syringe body is held in the safe position relative to the sheath by body of the syringe bearing directly against a bearing surface of the sheath.

In a particular embodiment of the invention, the head of the sheath serves to trigger the return member when the piston plunger is pushed into the body of the syringe.

BRIEF DESCRIPTION OF THE DRAWINGS

In other to make the invention better understood, there follows a description of an embodiment given as a non-limiting example and with reference to the accompanying drawing, in which.

MORE DETAILED DESCRIPTION

Figures 1, 2, 3:
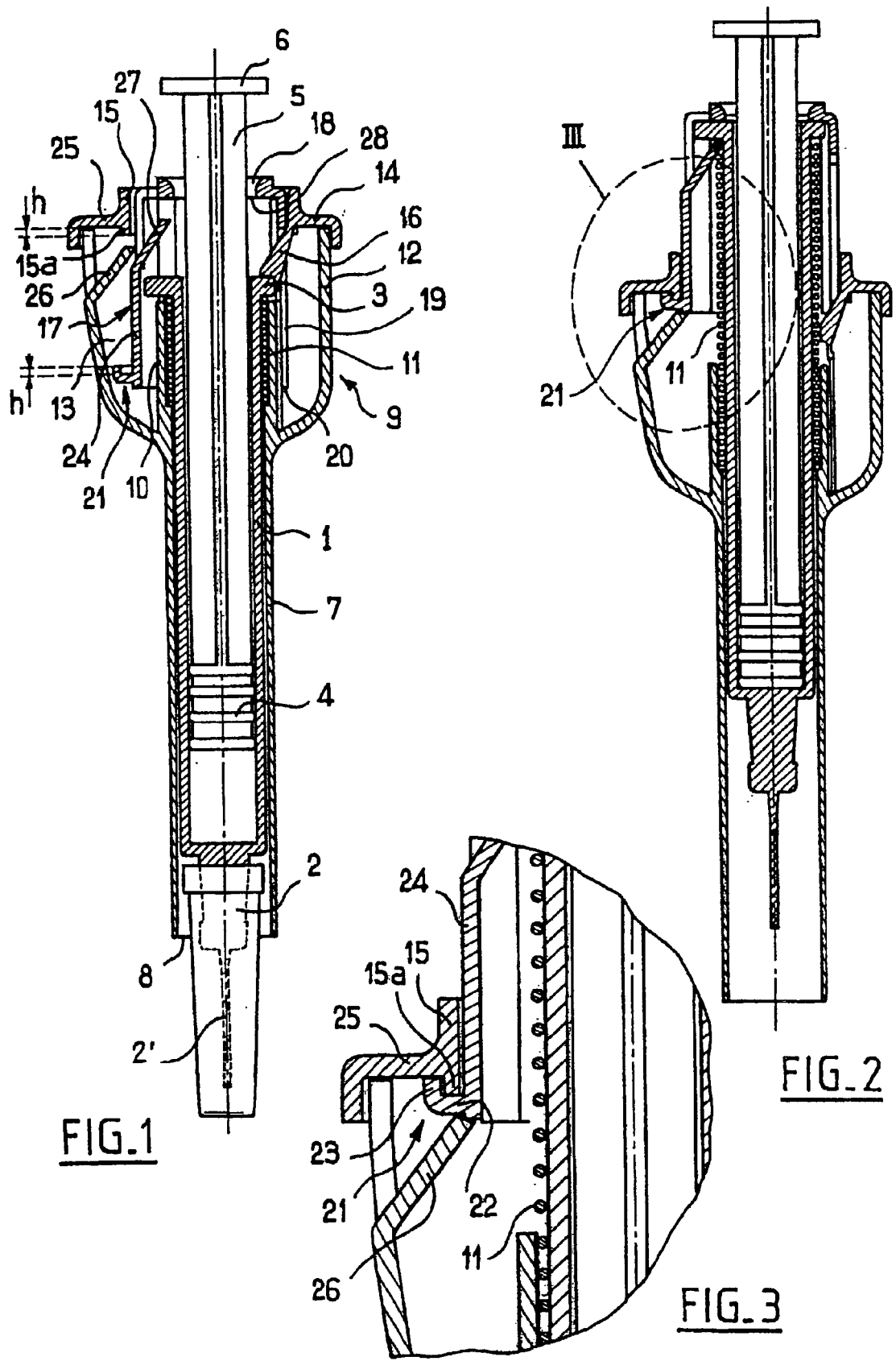
FIG. 1 is an axial section view of a safety device of the invention, containing a syringe.
FIG. 2 is a view analogous to FIG. 1, showing the syringe in the safe position.
FIG. 3 is a view on a larger scale showing a detail III of FIG. 2.

The syringe comprises a syringe body 1 provided at its front end with a needle carrier 2 on which there is mounted a needle 2'.

At its rear end, the syringe body has a collar 3.

A piston 4 is movable inside the syringe body and serves to inject the substance contained in the syringe body under drive from a piston plunger 5 projecting through the rear end of the syringe body and terminated in a pusher 6 against which the user of the syringe exerts pressure in order to inject the substance.

The syringe is placed in a safety device comprising a sheath constituted by a cylindrical portion 7 having a front end 8 and a head 9 opposite from the end 8.

The head 9 is made in two portions, one of which is axially movable so that the head 9 can be referred to as being "telescopic".

The stationary portion of the head 9 comprises a tubular portion 10 which is of larger inside dimensions than the cylindrical portion 7 of the sheath and houses a helical spring 11 which defines a cylindrical inside volume extending the inside cavity of the sheath in such a manner that the syringe body 1 engaged inside the sheath passes axially through the helical spring 11 without difficulty.

The collar 3 holds the spring in the compressed state.

The stationary portion of the head 9 also comprises an outer wall 12 which defines an annular chamber 13 around the tubular portion 10.

The wall 12 terminates at a ring 14 which, for ease of manufacture, is made separately and then fitted to the sheath, but which could alternatively have been made integrally therewith.

The ring 14 has a central passage 15 forming a neck and supporting a resilient tab 16 which serves as an axial abutment for the collar 3 of the syringe body 1, holding the body in the injection position inside the sheath, the spring 11 being compressed in its housing.

In this injection position, it can be seen that the needle carrier 2 is flush with the bottom end 8 of the sheath while the syringe body 1 is contained fully inside the sheath.

The moving portion of the head 9 is constituted by a cap 17 of generally cylindrical shape.

The cap 17 has a central bore 18 through which the piston plunger 5 can pass, and a longitudinal notch 19 extending from its bottom edge 20 and enabling the cap 17 to be engaged in the annular chamber 13 on either side of the resilient tab 16.

Away from the notch 19, the cap has a rim 21 at its bottom end 20, which rim is more clearly visible in the detail view of FIG. 3.

The rim 21 is constituted by a first wall portion 22 which extends radially outwards like a collar, and a second wall portion 23 which extends axially upwards, i.e. parallel to the wall 24 of the cap and away from the bottom end 20 thereof.

The radial wall 22 is at a distance from the bottom end 20 of the cap such that an angle is formed between the bottom face of the radial wall 22 and the outer face of the side wall 24.

The outside diameter of the cap 17 fits the inside diameter of the neck 15 which extends downwards below the closure wall 25 of the ring 14, by means of a portion 15a of height h substantially equal to the height of the side wall 23.

Opposite from the resilient tab 16, the wall 12 of the head 9 has a resilient tab 26 which extends towards the inside of the head so as to face the bottom end of the portion 15a of the neck 15, being situated at a distance therefrom corresponding substantially to the thickness of the radial wall 22.

The safety device operates as follows.

With the syringe in the injection position, as shown in FIG. 1, the user can push in the piston plunger 5 by exerting pressure on the pusher 6.

On reaching the end of its stroke, the piston 4 is in the vicinity of the needle carrier 2 and the pusher 6 is in contact with the cap 17.

The last part of the piston stroke entrains the cap 17 downwards, thereby causing it to be pushed into the head 9.

The notch 19 does not extend over the full height of the cap, so the side wall thereof moves the resilient tabs 16 away, thereby releasing the syringe body which can thus rise under drive from the helical spring 11.

Nevertheless, this upward movement does not take place so long as the user maintains sufficient pressure on the pusher 6.

When the user releases the pressure, the syringe body rises under drive from the spring.

Initially, the collar 3 pushes the cap upwards, bearing against an inwardly-directed resilient tab 27.

As the syringe body continues to move upwards, the cap rises and the side wall 23 comes into contact with the resilient tab 26 of the head.

Under drive from the spring, the resilient tab 26 retracts and allows the side wall 23 and the radial wall 22 to come into contact with the portion 15a of the neck 15.

The cap thus reaches the end of its stroke and is in its extended position.

The syringe body terminates its upward stroke when the collar 3 moves the resilient tab 27 away and comes to bear against the top wall 28 of the cap.

The resilient tab 27 then comes back into position and is received beneath the collar 3, thus preventing the syringe body 1 from moving relative to the cap.

With the syringe body being prevented from moving relative to the sheath, as explained in detail above, the syringe body is secured in a safe position inside the sheath with the needle carrier retracted into the sheath and with the needle not projecting beyond the bottom end 8 of the sheath.

The needle as retracted in this way avoids any risk of users coming into contact therewith or being pricked thereby.

It should be observed that, depending on the stiffness of the resilient tabs 26 and 27, it is possible, contrary to the description above, for the collar 3 initially to pass above the resilient tab 27 and subsequently for the side wall 23 and the radial wall 22 to pass above the resilient tab 26.

The axial locking achieved between the cap and the sheath is described below.

As can be seen in FIG. 3, the distance between the bottom end of the neck 15 and the end of the resilient tab 26 corresponds substantially to the thickness of the radial wall 22.

Consequently, the wall is wedged between the neck and the resilient tab 26, which becomes received in the angle formed beneath the wall 22.

In other words, the top and bottom faces of the radial wall 22 constitute two oppositely-directed axial abutments bearing against two axial abutments of the sheath constituted respectively by the bottom end of the neck 15 and by the end of the resilient tab 26.

Furthermore, the distance between the side walls 23 and 24 corresponds substantially to the thickness of the portion 15a of the neck 15, such that the inner face of the side wall 23 and the outer face of the side wall 24 constitute oppositely-directed lateral abutments bearing against opposite lateral abutments of the sheath constituted respectively by the inner and outer faces of the portion 15a of the neck 15.

Thus, the above-mentioned radial and axial abutments combine with one another to ensure that the cap 17 is secured reliably in the head on the sheath.

As a result, the device of the invention can be subjected to various radial and axial pressures without that interfering with the locking of the cap relative to the sheath, and consequently without that endangering the protection provided by the device when the syringe body is in the safe position.

It should be observed that the device of the invention is arranged so as to be capable of being used with a syringe of traditional type, without there being any need to modify the shape of the syringe.

Naturally, it will be understood that the above-described embodiment is not limiting in any way and can receive any desirable modification without thereby going beyond the ambit of the invention.

What is claimed is:

1. A safety device for a syringe, said syringe comprising:
   a body,
   a needle carrier mounted at one end of the body,
   a piston movable inside the body, and
   a piston plunger projecting from the body at its end opposite from the needle carrier and suitable for pushing the piston into the body towards the needle carrier, the device comprising:
   a sheath having a front end and a rear end, the syringe body being capable of sliding axially inside the sheath between an injection position in which the syringe body is fully contained within the sheath while the needle carrier of the syringe is flush with the front end of the sheath, and a safe position in which a portion of the syringe body projects from the rear end of the sheath while the needle carrier is set back from the front end of the sheath, the rear end of the sheath having a telescopic head, the telescopic head having a movable portion capable of taking up a retracted position in which it does not act on the syringe body when in the injection position, and an extended position in which it surrounds the portion of the syringe body that projects from the rear end of the sheath when in the safe position,
   a return member urging the syringe body towards the safe position, which return member is triggered automatically when the piston plunger is pushed into the body of the syringe,
   a combination for locking the telescopic head in the extended position, comprising two oppositely-directed axial bearing surfaces of the movable portion of the telescopic head which bear against two oppositely-directed axial bearing surfaces of the sheath, and two oppositely-directed lateral bearing surfaces of the movable portion of the telescopic head which bear against two oppositely-directed lateral bearing surfaces of the sheath, one of said lateral bearing surfaces of the movable portion of the telescopic head being radially outside one of said lateral bearing surfaces of the sheath.

2. A device according to claim 1, wherein the telescopic head prevents the syringe body from moving axially relative to the sheath.

3. A device according to claim 1, wherein the sheath has a bearing surface for preventing the syringe body from moving when in the safe position.

4. A device according to claim 1, wherein the head of the sheath serves to trigger the return member when the piston plunger is pushed into the body of the syringe.

5. A device according to claim 1, wherein the two oppositely-directed axial bearing surfaces of the head are constituted by the top and bottom faces of a radial wall that extend outwards so as to form a collar on a side wall of a cap constituting the movable portion of the telescopic head, and wherein the two oppositely-directed lateral abutment surfaces of the head are constituted by an inner face of a side wall extending from the radial wall and by the outer face of the side wall of the cap.

6. A device according to claim 5, wherein the oppositely-directed lateral abutment surfaces of the sheath are constituted by the inner and outer faces of the bottom end of a neck in which the moving cap slides, and wherein the oppositely-directed axial abutment surfaces of the sheath are constituted by the bottom end of the neck and by the end of a resilient tab situated facing said bottom end of the neck.

* * * * *